United States Patent
Mizumoto et al.

(10) Patent No.: US 6,803,054 B2
(45) Date of Patent: *Oct. 12, 2004

(54) TECHNICAL FIELD

(75) Inventors: Takao Mizumoto, Yaizu (JP);
Yoshinori Masuda, Yaizu (JP); Atsushi Kajiyama, Yaizu (JP); Masahiro Yanagisawa, Yaizu (JP); Janaki Ram Nyshadham, Palo Alto, CA (US)

(73) Assignees: Yamanouchi Pharmaceutical Co., Ltd., Tokyo (JP); Yamanouchi Pharma Technologies, Inc., Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/453,422

(22) Filed: Jun. 2, 2003

(65) Prior Publication Data

US 2003/0203022 A1 Oct. 30, 2003

Related U.S. Application Data

(63) Continuation of application No. 09/646,249, filed as application No. PCT/JP98/04592 on Oct. 13, 1998, now Pat. No. 6,589,) 554.
(60) Provisional application No. 60/078,761, filed on Mar. 16, 1998.

(51) Int. Cl.$^7$ .............................................. A61K 9/20
(52) U.S. Cl. ........................................................ 424/464
(58) Field of Search ................................ 424/464, 400, 424/465, 489

(56) References Cited

U.S. PATENT DOCUMENTS 5,576,014 A 11/1996 Mizumoto et al.
6,589,554 B1 * 7/2003 Mizumoto et al. .......... 424/465

FOREIGN PATENT DOCUMENTS

EP 0651997 A1 5/1995
JP 48-103717 12/1973

(List continued on next page.)

OTHER PUBLICATIONS

Sebhatu, Elamin and Ahlneck; Effect Moisture Sorption on Tabletting Characteristics of Spray Dried (15% Amorphous) Lactose; Pharmaceutical Research; 1994, pp. 1233–1238, vol. 11, No. 9; Plenum Publishing Corp., New York.

(List continued on next page.)

*Primary Examiner*—Thurman K. Page
*Assistant Examiner*—Robert M. Joynes
(74) *Attorney, Agent, or Firm*—Townsend and Townsend and Crew LLP

(57) ABSTRACT

The present invention relates to a quick disintegrating tablet in buccal cavity, comprising: a mixture, comprising a drug, a sugar (A), and an amorphous sugar (B), and after it is forming a tablet, it is humidified and dried. In particularly, the present invention relates to a quick disintegrating tablet in buccal cavity comprising: a mixture; comprising a drug, a sugar (A), and an amorphous sugar (B) which an amorphous-forming sugar in crystalline state is dissolved in a medicinally permitted solvent, the amorphous sugar is obtained from this solution by removing the solvent, and after it is forming a tablet, and it is humidified and dried.

Figure 1:
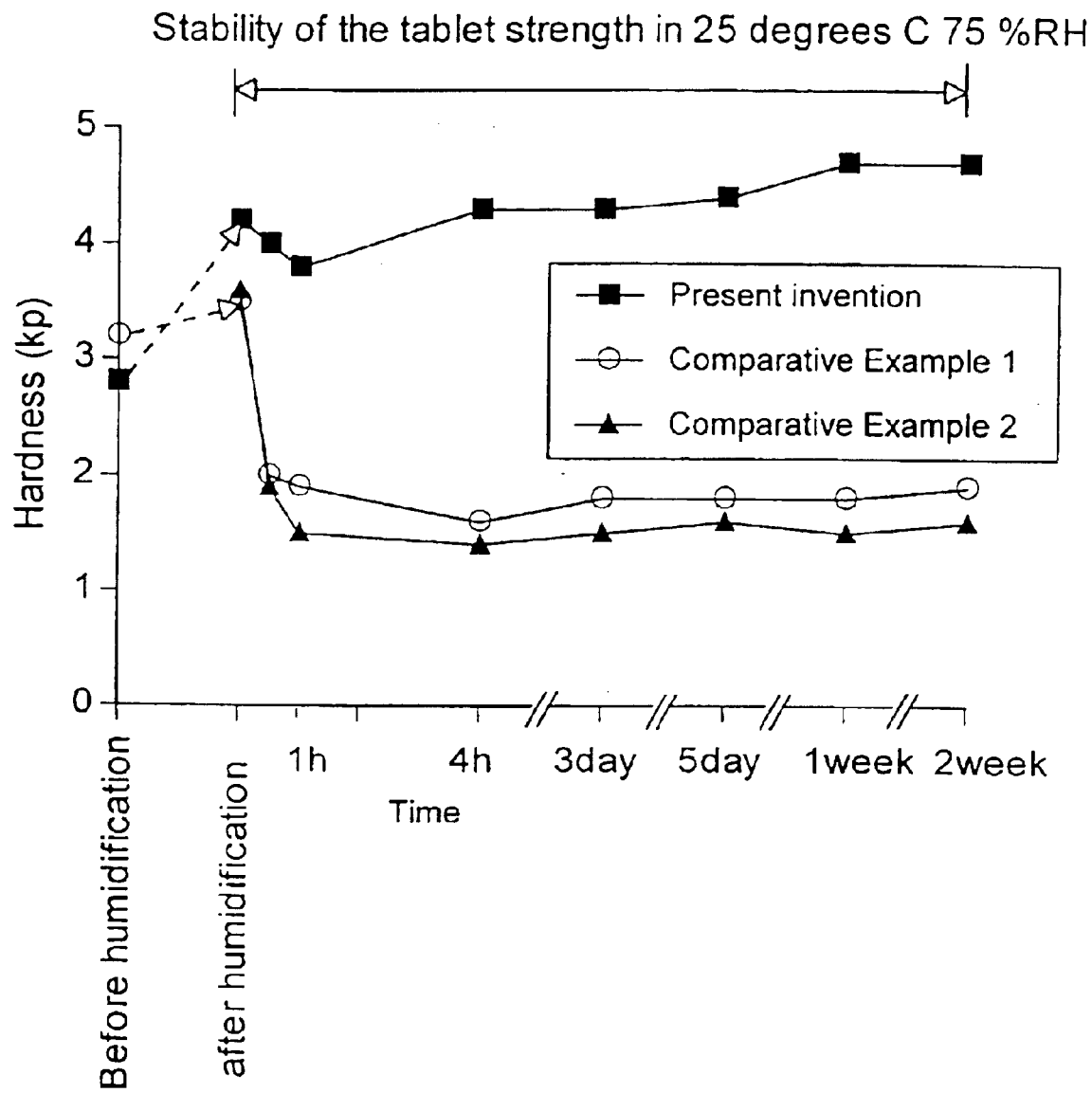

The tablet in the present invention is to provide stability against moisture at preserved, because the amorphous sugar changed to the crystalline state in a nonreversible reaction after it is humidified and dried in a manufacturing process. The tablet in the present invention is to further provide a design for the pharmaceutical preparation with respect to the stability of a drug, because the tablet is manufactured by one kind of a sugar and an amorphous sugar. Furthermore, the tablet in the present invention is to provide a production process by utilizing a common granulating machine and by utilizing a common tablet machine.

38 Claims, 1 Drawing Sheet

FOREIGN PATENT DOCUMENTS

| | | |
|---|---|---|
| JP | 60-4124 | 1/1985 |
| JP | 61-194016 | 8/1986 |
| JP | 9-48726 | 2/1997 |
| JP | 948726 * 2/1997 | ............ A61K/9/20 |

OTHER PUBLICATIONS

Vromans, Bolhuis, Lerk, Van De Biggelaar, Bosch; Studies on tableting properties of lactose; Int. Journal of Pharmaceutics, 1987, pp. 29–37, vol. 35; Elsevier Science Publishers B.V.

* cited by examiner

TECHNICAL FIELD

CROSS-REFERENCE TO RELATED APPLICATIONS

This is a continuation of allowed U.S. patent application Ser. No. 09/646,249, filed Sep. 14, 2000, now U.S. Pat. No. 6,589,554, which is a 371 of PCT/JP98/04592, filed Oct. 13, 1998, which claims benefit of 60/078,761, filed Mar. 16, 1998.

TECHNICAL FIELD

The present invention relates to a quick disintegrating tablet in buccal cavity and production process thereof.

BACKGROUND OF THE INVENTION

As for the pharmaceutical dosage forms for oral use, a tablet, a capsule, a granule, a powder and the like are mentioned. However, these dosage forms will have some issues if a patient takes them. For instance, regarding a tablet or a capsule, if the patient is a person of advanced age or a child, there are some cases that they dislike to take the pharmaceutical preparation because it is difficult for them to swallow it or the preparation will stick in the throat or the esophagus of them. In addition, regarding a granule or a powder, in some cases they dislike to take the preparation under the reason that it is difficult for them to swallow it with its remaining in buccal cavity or the reason that they will choke when taking the dosage. Since a compliance to take the pharmaceutical preparation is caused to fall in these cases, it is desired to take easily the pharmaceutical dosage forms, and as a result a disintegrating preparation in buccal cavity has been studied and developed.

For instance, "Zydis®" has been developed up to the product by R. P. Schere Corp. However, since this preparation is produced by means of lyophilization method, a special manufacturing equipment such as a lyophilization machine is needed. Additionally, this preparation cannot be taken over from the pocket of PTP, "Press Through Package", under the reason that the tablet strength is small. Furthermore, it is so difficult for the aged to take out the preparation from package that it is not satisfied with the aged.

Several quick disintegrating tablets in buccal cavity, which is manufactured by means not of lyophilization method but of tableting method, have been reported. For instance, JP 6-218028-A (Corresponding to EP 590,963) discloses a quick disintegrating tablet in buccal cavity which is manufactured by compressing the moisturized powder being mixed with a drug, an excipient, a binder agent and the like using water or the like, afterwards by drying the compression molding. However, it is necessary to have a special tableting machine spraying a fluidizer on the surface of a tablet before compression for the avoidance of the issues at the compression molding. JP 5-271054-A (corresponding to EP 553,777) discloses a quick disintegrating tablet in buccal cavity which is manufactured by compressing the mixture comprising a drug, a sugar and water which is added so much as to moisture said sugar at low compression pressure, and by drying said tablet. WO93/15724 (corresponding to EP 627,218) also discloses a quick disintegrating tablet, which is manufactured by compression with humidification and drying. However, there are some issues in these methods, for instance, a sticking at compressing with moisture.

In addition, WO95/20380 (corresponding to U.S. Pat. No. 5,576,014) discloses a quick disintegrating tablet in buccal cavity in which the invention has been made by one of the present inventors. This tablet is manufactured by means that a small moldability sugar is granulated by a high moldability sugar and afterwards that these granules are compressed by an ordinal tableting machine. It is thought that there is little trouble in practice by this production method, however, it is necessary to utilize at least two kinds of sugars, if there is a case that there is a restriction to a kind of sugar added, for the counter action between a drug and said sugar (for example, degradation of drug). Therefore, a new quick disintegrating tablet in buccal cavity and production process thereof are desired even at this present, for instance, this tablet is manufactured and to obtain by using one kind of sugars.

Furthermore, regarding a quick disintegrating tablet in buccal cavity, a patent application or an article discloses the following production process proposed.

For instance, JP 9-48726-A discloses the method which a composition of the mixture consisting of a drug, a sugar and/or hydrophilic polymer is taken into a molding, and the mixture is compressed at low compression pressure, and the molding is under humidification and drying. However, this method is to improve the strength of tablet surface in particular by moisture of water-soluble polymer, it is possible to introduce the adhesion between tablets.

A method that a mixture consisting of an amorphous sucrose which is obtained by lyophilization method utilizing a sucrose solution, a drug and mannitol is molded into a tablet by a rotally tableting machine, and the obtained tablet is preserved under the controlled circumstance (at 25° C., 34% RH) is proposed (abstract of the 13$^{th}$ Japan pharmacological pharmacy, p.113, published Mar. 5, 1998). However, a sugar is an amorphous sugar that is manufactured in further detail by lyophilization method, but sugars outsides sucrose is not described in the article.

DISCLOSURE OF THE INVENTION

An object of the present invention is to provide a quick disintegrating tablet in buccal cavity and production thereof in which tablets are manufactured with the normal granulator and tablet machine, with tablet strength being heightened to make a more stable formulation.

The present inventors examined the physiological characterization of sugar in a result to find that a kind of sugars can be changed to an amorphous state when the sugar solution is spray-dried, or the sugar solution is used in granulation as a binding agent. The present inventors further investigated to find that when an amorphous sugar was treated under humidification and drying, the tablet strength was increased by changing the amorphous sugar to a crystal state and that a disintegrating preparation in buccal cavity with the desired tablet strength was obtained and have completed the present invention.

That is, the present invention relates to a quick disintegrating tablet in the buccal cavity, comprising: a drug, a sugar (A), and an amorphous sugar (B), in which, after forming the tablet, it is humidified and dried. In more detail, the present invention relates to a quick disintegrating tablet in the buccal cavity, comprising: a mixture, comprising: a drug, a sugar (A), and an amorphous sugar (B) which is obtained by dissolving a crystalline sugar capable of becoming amorphous in a medicinally permitted solvent and then removing the solvent from the solution and drying, in which after forming the tablet, it is humidified and then dried. Furthermore, the present invention relates to a quick disintegrating tablet in the buccal cavity, comprising: a mixture, comprising: a drug, a sugar (A), and an amorphous sugar (B) which is obtained by dissolving a crystalline sugar capable of becoming amorphous in a medicinally permitted solvent, and the solution is then sprayed and dried, and after forming the tablets, it is humidified and then dried. In particular, the present invention relates to a quick disintegrating tablet in buccal cavity, comprising: a crystalline sugar capable of becoming amorphous is dissolved in a medicinally permitted solvent; the solution is sprayed on a drug and/or a sugar (A) to coat and/or granulate; and after forming a tablet, it is humidified and dried.

For the drug to be used in the present invention, there are no particular limitations as long as it is a substance which is used as a pharmaceutical active ingredient. Examples of pharmaceutical active ingredients include: sedative hypnotics, sleep inducers, anti-anxiety drugs, anti-epileptics, anti-depressants, anti-Parkinson drugs, psychoneural drugs, drugs acting on the central nervous system, local anesthetics, skeletal muscle relaxants, autonomic nervous system drugs, anti-fever analgesics anti-inflammatory drugs, anti-convulsants, anti-vertigenous drugs, cardiac drugs, drugs for arrhythmia, diuretics, blood pressure lowering drugs, vasoconstrictors, vasodilators, drugs for circulatory organs, hyperlipidemia drugs, respiratory stimulant, anti-tussive, expectorants, anti-tussive expectorants, bronchodilators, stegnotic, peptic ulcer drugs, stomach digestive drugs, antacids, laxatives, choleretics; drugs for the digestive tract, adrenal hormone drugs, hormone drugs, urinary tract drugs, vitamins, hemostatic drugs, liver drugs, gout treatment drugs, drugs for diabetes, anti-histamines, antibiotics, anti-bacterial agents, anti-malignant tumor drugs, chemotherapy drugs, multi-purpose cold medicines, tonic medicines, osteoporosis drugs, and the like. There are no particular limitations on the amount of these drugs to be mixed as long as it is the usual effective treatment amount. It should be around 50 weight/weight % or below of the entire tablet, and is preferably 20 weight/weight % or below.

In case that the present invention is applied to a drug having unpleasant taste, the drug is preferred to be treated in a preferably taste masking method (for instance, WO92/09275).

In case of that the present invention is performed for a drug desired to be sustained, the drug is preferred to be treated in a preferably sustained-release method (for instance, CA2038400-0), to obtain a particle which is controlled a drug release in a known manner in itself.

Furthermore, the preparation of the present invention can be also applied to a drug which is needed to be absorbed through a membrane of buccal cavity, since the preparation of the present invention is taken by a patient with disintegrating and dissolving in buccal cavity.

There are no particular limitations on sugar (A) which is to be used in the present invention as long as it is one which is normally medicinally permitted. Sugar (A) is preferably a sugar or sugar-alcohol which dissolves in the mouth. Examples include lactose, glucose, trehalose, mannitol, erythritol, and the like. Sugar (A) can be one type or two or more types combined. Furthermore, since sugar (A) functions as an excipient which dissolves inside the buccal cavity, the amount of sugar (A) to be added to the quick disintegrating tablet of the present invention is not particularly limited as long as it is an effective amount in order to achieve this function in the quick disintegrating tablet. The amount of sugar (A) to be added is dependent on the amount of drug and can be adjusted appropriately. In other words, when the amount of drug is small, the amount of sugar (A) to be added becomes large, and if the amount of drug is large, the amount of sugar (A) to be added becomes small. The amount of sugar (A) to be added is also dependent on the size of the tablet. The amount of sugar (A) can be adjusted as a ratio with the other excipients.

The "amorphous sugar (B)" of the present invention signifies a sugar which is medicinally usually permitted and which is amorphous or which is capable of becoming amorphous. For example, an amorphous sugar (B) can be obtained by dissolving a crystalline sugar capable of becoming amorphous in a medicinally permitted solvent such as water and alcohol and the like, and then obtained by removing the solvent from this solution, and drying. There are no particular limitations for the method of removing the solvent as long as it is a method normally implemented in the pharmaceutical manufacturing process. For example, these methods include spray drying method, freeze-drying method, or various granulating methods such as fluidized-bed granulating method, vertical granulating method, tumbling granulating method. From a production standpoint, spray drying method or the various granulating methods are preferred. Among the various granulating methods, a method is preferred wherein: a crystalline sugar capable of becoming amorphous in a medicinally permitted solvent such as water, alcohol, and the like; this is used as a binding agent; this becomes amorphous when it is sprayed by a twin fluid nozzle and coats and/or granulates the drug and/or the sugar. Here, a crystalline sugar capable of becoming amorphous can be dissolved in a medicinally permitted solvent. This solution can be sprayed against the drug and/or the sugar (A), and they can be coated and granulated with an amorphous sugar (B). Examples of amorphous sugars (B) include glucose, lactose, maltose, sorbitol, trehalose, lactitol, fructose, and the like. This amorphous sugar (B) can be of one type or be a combination of two or more types. In the present invention, "amorphous sugar" signifies a sugar which is materially amorphous or which is capable of becoming amorphous. In the process of becoming amorphous, the present invention also includes states where a portion is not amorphous. The amount of amorphous sugar (B) to be added is 2–20 weight/weight % with respect to the previous sugar (A), or 2–20 weight/weight % of the entire tablet.

As for the advantage for utilizing an amorphous sugar in the present invention, it is easy to increase tablet strength by steps of humidification and drying. Since an amorphous sugar has a low critical moisture, the tablet can be treated at the low moisture level such that an amorphous sugar can adsorb. In addition, the moisture absorbed in a humidification process dissolve a part of surface of sugar particles around, afterwards in a drying process, the tablet strength can increase because of the re-attachment of between sugar particles. On the other hand, to the contrally to the present invention, it is easily to be predicted that the production process has some difficulties, for instance, in case that the sugar consists of sugars in a crystalline state, since the sufficient moisture adsorption will not happen at a low humidification condition, the tablet strength will not increase, in case at a high humidification condition, the adhesion of between tablets will happen and it is easily predictable for actual manufacturing to have difficulty.

As for the other advantage for utilizing amorphous sugar in the present invention, since a sugar in amorphous state is changed to a crystalline state in a humidification and drying process unreversibly, a dried tablet has a high critical moisture point. As a result, said tablet can maintain a tablet strength against the moisture in the stored condition.

Furthermore, since one kind of sugar consisting of crystalline state and amorphous state can manufacture a quick disintegrating tablet in buccal cavity to avoid a restriction for choosing a sugar which do not happen the changes against a drug.

In the present invention, "forming" signifies forming into a tablet or the like with a pressure equal to or greater than the pressure required to maintain the desired shape. In the forming process, a normal tablet machines can be used. Examples include a single tablet machine or rotary tablet machine.

In the present invention, "humidifying", when implemented in combination with the next step of drying, is for increasing the tablet strength, the humidifying conditions being determined by the apparent critical relative humidity of the mixture of a drug, a sugar (A), an amorphous sugar (B), and signifies increasing the humidity to greater than or equal to the critical relative humidity of this mixture. For example, the humidity is 30–100 RH %, and is preferably 50–90 RH %. At this time, temperature is 15–50° C., and preferably 20–40° C. The point of the humidifying process of the present invention is to convert sugar in the amorphous state to a crystalline state, to heighten the tablet strength, and to make the tablet more stable.

In the present invention, "drying" is implemented in order to remove the water absorbed by the humidifying the amorphous sugar. There are no particular limitations for the drying conditions as long as they are the usual conditions for removing water content. For example, it should be 10–100° C. and is preferably 20–60° C.

The quick disintegrating tablet in buccal cavity can contain various medicinally permitted excipients such as disintegrating agents, stabilization agents, binding agents, diluting agents, lubricating agents, and the like.

The production method of the quick disintegrating tablet in buccal cavity is described below.

For the production method of the present invention, a drug, a sugar (A), and an amorphous sugar (B) are mixed, and after forming the mixture into a tablet, it is humidified and dried. In more detail, in the production method of the present invention, a mixture of the following is formed: a drug, a sugar (A), and an amorphous sugar (B) which is obtainable by dissolving a crystalline sugar capable of becoming amorphous in a medicinally permitted solvent and removing the solvent from the solution and drying, and the tablet is humidified and dried. Furthermore, in the production method of the present invention, a mixture of the following is formed into a tablet: a drug, a sugar (A), and an amorphous sugar (B) which is obtainable by dissolving a crystalline sugar capable of becoming amorphous in a medicinally permitted solvent and spraying and drying the solution, and the tablet is humidified and dried. In particular, in the production method of the present invention, after dissolving a crystalline sugar capable of becoming amorphous in a medicinally permitted solvent and by using a binding agent, the solution is sprayed with a twin fluid nozzle or the like against a drug and/or sugar (A), and after forming a coated product and/or granulated product by coating and/or granulating with an amorphous sugar (B), and after forming a tablet, it is humidified and dried.

Here, the definitions and the preferred embodiments of the "drug", "sugar (A), and "amorphous sugar (B)", as well as the processing steps for the production of quick disintegrating tablet in buccal cavity including "forming ", "humidifying", and "drying" are described previously.

Furthermore, as a method for removing the solvent in the present invention, there are no particular limitations as long as it is a method implemented in the normal manufacturing process. For this method, examples include spray drying method, freeze-drying method, or various granulating methods such as fluidized-bed granulating method, vertical granulating method, tumbling granulating method, or the like. From the standpoint of production, the spray drying method or the various granulating methods are preferred. Among these, in the various granulating methods, a method is preferred, wherein: a crystalline sugar capable of becoming amorphous and which is dissolved in a medicinally permitted solvent such as water or alcohol is used as a binding agent, and it becomes amorphous when spraying and coating or granulating with a twin fluid nozzle or the like against drug and/or sugar (A). Here, crystalline sugar which is capable of becoming amorphous can be dissolved in a medicinally permitted silvent, and the solution can be sprayed, and the drug and/or sugar (A) can be coated and granulated with amorphous sugar (B).

In the production method of the present invention, various medicinally permitted excipients such as disintegrating agents, stabilizing agents, binding agents, diluents, lubricants, or the like can be added to any of the production steps.

BREIF DESCRIPTION OF DRAWINGS

FIG. 1 shows the stability of the tablet strength in the present invention. In the FIGURE, the horizontal axis represents to time and the vertical axis represents to tablet strength.

BEST MODE FOR CARRYING OUT THE INVENTION

The present invention will be explained further by citing examples. The present invention is not limited to these embodiments. Furthermore, regarding the tablet of the present invention, the tablet strength and time of disintegration in the buccal cavity have been evaluated. Because it is considered to have little influence on the evaluation categories, the drug is not always included.

EXAMPLE 1

Mannitol 602 g and lactose 602 g were mixed. This was passed through a sieve (14 mesh). 433 g of glucose solution (15 w/v %) was used as a binding agent for this mixture, and the mixture was granulated in a fluidized-bed granulator. Up to 157 g of the solution was used to coat the above mixture at a spray pressure of 2.5 kg/cm$^2$. Afterwards, it was granulated with spray pressure 1.5 kg/cm$^2$. After drying the granule, peppermint flavor 10 g , stearic acid 12 g, magnesium stearate 10 g were combined. Rotary tablet machine was used to manufacture tablets which were 540 mg per one tablet (tablet hardness 1.4 kp (n=5)). Next, this tablet was humidified and heated for 20 minutes in a thermo-hygrostat at 35° C., 85% RH. Afterwards, it was dried for 15 minutes at 50° C. (humidity 30%), and the tablet of the present invention was achieved. The obtained tablet had hardness of 9.1 kp, and buccal cavity disintegrating time of 17 seconds.

EXAMPLE 2

175 g of a lactose solution (10 w/v %) was a binding agent for 350 g of lactose (Domo milk Corp.). This was granulated in a fluidized-bed granulator (Ohkawara Seisakusho). Up to 70 g of the previous solution was used to coat the lactose with a spray pressure of 2.5 kg/cm$^2$. Afterwards, it was granulated with a spray pressure 1 kg/cm$^2$. After drying the granule, 0.5% magnesium stearate was mixed with the granule. Tablets ((phi 10 mm, 10 mmR), tablet hardness 2.3 kp (n=5)) of 300 mg per tablet were produced using a rotary tablet machine. Next, the tablet was stored under heated humidified conditions of 25° C./70% RH for 19 hours, using a thermo-hygrostat (Tabiespec Corp., PR-35C). Afterwards it was dried for 2 hours at 25° C. (humidity 50%). The tablet of the present invention was obtained. The obtained tablet had a hardness of 4.1 kp (n=5) and a buccal cavity disintegration time of 20 seconds.

EXAMPLE 3

378 g of mannitol (Towa Chemical Industry Corp.) was passed through a sieve (20 mesh). Afterwards, this was granulated in a fluidized bed granulator (Ohkawara Seisakusho) with 133 g of an aqueous solution of hydrated crystalline glucose (Nippon Shokuhin Kako Corp.) (15 w/v %) as a binding agent. Up to 50 g of the previous solution was used to coat the mannitol with a spray pressure of 2.5 kg/cm$^2$. Afterwards, it was granulated with a spray pressure 1.5 kg/cm$^2$. At this time, the disappearance of the absorption peak derived from glucose crystals (i.e. glucose is amorphous) was confirmed using a differential scanning calorimeter (DSC for short). 0.5% magnesium stearate was mixed with the granule. Tablets ((phi 8 mm, 9.6 mmR), tablet hardness 2.0 kp (n=5)) of 150 mg per tablet were produced using a rotary tablet machine with a compression pressure of approximately 0.18 ton/punch. Next, the tablet was stored under heated humidified conditions of 25° C./70% RH for 24 hours, using a thermo-hygrostat (Tabiespec Corp., PR-35C). Afterwards it was dried for 2 hours at 30° C. (humidity 40%). The tablet of the present invention was obtained. The obtained tablet had a hardness of 5.4 kp (n=5) and a buccal cavity disintegration time of 20 seconds. Furthermore, by measuring the obtained tablet with DSC, it was confirmed that an absorption peak derived from glucose crystals was present and glucose had crystallized.

EXAMPLE 4

425.25 g of erythritol (Nikken Chemical Corp.) was passed through a sieve (20 mesh). Afterwards, this was granulated with a fluidized-bed granulator (Ohkawara Seisakusho) with 150 g of maltose (Product name Sanmalt-S, Hayashibara Shoji Corp.) aqueous solution (15 w/v %) as a binding agent. Up to 60 g of the previous solution was used to coat erythritol with a spray pressure of 3.0 kg/cm$^2$. Afterwards, it was granulated with a spray pressure 1.4 kg/cm$^2$. 0.5 % magnesium stearate was mixed with the granule. Tablets ((phi 8 mm, 9.6 mmR), tablet hardness 2.0 kp (n=5)) of 150 mg per tablet were produced using a rotary tablet machine with a compression pressure of approximately 0.3 ton/punch. Next, the tablet was stored under heated humidified conditions of 25° C./70% RH for 24 hours, using a thermo-hygrostat (Tabiespec Corp., PR-35C). Afterwards, it was dried for 2 hours at 30° C. (humidity 40%). The tablet of the present invention was obtained. The obtained tablet had a hardness of 7.6 kp (n=5) and a buccal cavity disintegration time of 20 seconds.

EXAMPLE 5

360 g of mannitol (Towa Chemical Industry) was passed through a sieve (20 mesh). Afterwards, this was granulated in a fluidized-bed granulator (Ohkawara Seisakusho) with 266 g of fructose (Hayashibara Shoji Company) aqueous solution (15 w/v %) as a binding agent. With respect to this granule, it was confirmed by DSC that the absorption peak derided from fructose crystals disappeared and the fructose was amorphous. 0.5% magnesium stearate was mixed with the granule. Tablets ((phi 8 mm, 9.6 mmR), tablet hardness 1.1 kp (n=5)) of 150 mg per tablet were produced using a rotary tablet machine with a compression pressure of approximately 0.06 ton/punch. Next, the tablet was stored under heated humidified conditions of 25° C./70% RH for 12 hours, using a thermo-hygrostat (Tabaiespec Corp., PR-35C). Afterwards, it was dried for 2 hours at 40° C. The tablet of the pressure invention was obtained. The obtained tablet had a hardness of 5.6 kp (n=5) and a buccal cavity disintegration time of 15 seconds.

EXAMPLE 6

133 g of a lactitol (Towa Chemical Industry Corp., Milhen) aqueous solution (15 w/v %) was a binding agent for 380 g of lactose (Domo milk Corp.). This was granulated with a fluidized-bed granulator (Ohkawara Seisakusho). With respect to this granule, it was confirmed by DSC that the absorption peak derived from lactitol crystals disappeared had the lactitol was amorphous. 0.5% magnesium stearate was mixed with the granule. Tablets ((phi 8 mm, 9.6 mmR), tablet hardness 1.0 kp (n=5)) of 150 mg per tablet were produced using a rotary tablet machine with a compression pressure of approximately 0.1 ton/punch. Next, the tablet was stored under heated humidified conditions of 25° C./70% RH for 12 hours, using a thermo-hygrostat (Tabaiespec Company, PR-35C). Afterwards it was dried for 2 hours at 40° C. The tablet of the present invention was obtained. The obtained tablet had a hardness of 3.7 kp (n=5) and a buccal cavity disintegration time of 15 seconds. Furthermore, by measuring the obtained tablet with DSC, it was confirmed that an absorption peak derived from lactitol crystals was present and lactitol had crystallized.

EXAMPLE 7

133 g of a trehalose (Hayashibara Shoji) aqueous solution (15 w/v %) was a binding agent for 380 g of hydrated crystalline glucose (Nippon Shokuhin). This was granulated with a fluidized-bed granulator (Ohkawara Seisakusho). 0.5% magnesium stearate was mixed with the granule. Tablets ((phi 8 mm, 9.6 mmR), tablet hardness 1.0 kp (n=5)) of 150 mg per tablet were produced using a rotary tablet machine with a compression pressure of approximately 0.1 ton/punch. Next, the tablet was stored under heated humidified conditions of 25° C./70% RH for 12 hours, using a thermo-hygrostat (Tabaiespec Cor., PR-35C). Afterwards, it was dried for 2 hours at 40° C. The tablet of the present invention was obtained. The obtained tablet had a hardness of 4.3 kp (n=5) and a buccal cavity disintegration time of 20 seconds.

EXAMPLE 8

40 g famotidine, 336.8 g of erythritol (Nikken Chemical Corp.) were passed through a sieve (20 mesh). Afterwards, this was granulated with a fluidized-bed granulator (Ohkawara Seisakusho) with 100 g of a lactitol (Towa Chemical Industry Corp.) aqueous solution (20 w/v %) as a binding agent. 0.8% calcium stearate was mixed with the granule. Tablets ((phi 8.5 mm, 10.2 mmR), tablet hardness 1.1 kp (n=5)) of 200 mg per tablet were produced using a rotary tablet machine with a compression pressure of approximately 0.14 ton/punch. Next, the tablet was stored under heated humidified conditions of 25° C./80% RH for 12 hours, using a thermo-hygrostat (Tabaiespec Company, PR-35C). Afterwards, it was dried for 2 hours at 30° C.

(humidity 40%). The tablet of the present invention was obtained. The obtained tablet had a hardness of 6.2 kp (n=5) and a buccal cavity disintegration time of 20 seconds.

EXAMPLE 9

100 g acetaminophen, 227 g lactose (Domo milk Company) were passed through a sieve (20 mesh). Afterwards, this was granulated in a fluidized-bed granulator (Ohkawara Seisakusho) with 100 g of a trehalose (Hayashibara Shoji) solution (20 w/v %) as a biding agent 0.5% magnesium stearate was mixed with the granule. Tablets ((phi 8.5 mm, 10.2 mmR), tablet hardness 1.4 kp (n=5)) of 200 mg per tablet were produced using a rotary tablet machine with a compression pressure of approximately 0.3 ton/punch. Next, the tablet was stored under heated humidified conditions of 25° C./80% RH for 12 hours, using a thermo-hygrostat (Tabaiespec Companu, PR-35C). Afterwards, it was dried for 2 hours at 30° C. (humidity 40%). The tablet of the present invention was obtained. The obtained tablet had a hardness of 3.1 kp (n=5) and a buccal cavity disintegration time of 25 seconds.

EXAMPLE 10

An aqueous solution (25w/v %) of trehalose (Hayashibara Shoji) was spray dried using a spray dryer (Daiwa Kagaku DL-41). An amorphous trehalose powder was obtained. 5 parts trehalose powder to 95 parts mannitol (Towa Chemical Industry Corp.) were mixed in a mortar. This mixture was made into tablets of one tablet 150 mg ((phi 8 mm, 9.6 mmR), tablet hardness 1.1 kp (n=5)) us tablet was stored under heated humidified conditions of 25° C./80% RH for 12 hours, using a thermo-hygrostat (Tabaiespec Corp., PR-35C). Afterwards, it was dried for 2 hours at 30° C. (humidity 40%). The tablet of the present invention was obtained. The obtained tablet had a hardness of 6.1 kp (n=5) and a buccal cabity disintegration time of 15 seconds.

EXAMPLE 11

380 g of mannitol (Towa Chemical Industry) was passed through a sieve (20 mesh). Afterwards, this was granulated in a fluidized-bed granulator (Ohkawara Seisakusho) with 133 g of trehalose (Hayashibara Shoji Company) aqueous solution (15 w/v %) as a binding agent. 0.5% magnesium stearate was mixed with the granule. Tablets ((phi 8 mm, 9.6 mmR), tablet hardness 2.8 kp (n=5)) of 150 mg per tablet were produced using a rotary tablet machine with a compression pressure of approximately 0.4 ton/punch. Next, the tablet was stored under heated humidified conditions of 25° C./70% RH for 12 hours, using a thermo-hygrostat (Tabaiespec Corp., PR-35C). Afterwards, it was dried for 2 hours at 30° C. (humidity 40%). The tablet of the pressure invention was obtained. The obtained tablet had a hardness of 3.9 kp (n=5).

COMPARATIVE EXAMPLE 1

A sugar (B) is utilized xyritol which does not change into amorphous state in replacing trehalose in Example 11. In particularly, 380 g of a mannitol (Towa Chemical Industry Corp.) was passed through a sieve (20 mesh). Afterwards, this was granulated in a fluidized-bed granulator (Ohkawara Seisakusho) with 130 g of a xyritol (Towa Chemical Industry Corp.) aqueous solution (15 w/v %) as a binding agent. With respect to this granule, it was confirmed by DSC that the absorption peak derided from xyritol crystals remained and the xyritol was in crystalline state. 0.5% magnesium stearate was mixed with the granule. This was granulated with a fluidized-bed granulator (Ohkawara Seisakusho). 0.5% magnesium stearate was mixed with the granule. Tablets ((phi 8 mm, 9.6 mmR), tablet hardness 3.2 kp (n=5)) of 150 mg per tablet were produced using a rotary tablet machine with a compression pressure of approximately 0.8 ton/punch. Next, the tablet was stored under heated humidified conditions of 25° C./70% RH for 12 hours, using a thermo-hygrostat (Tabaiespec Cor., PR-35C). Afterwards, it was dried for 2 hours at 30° C. (humidity 40%). The tablet of the Comparative Example was obtained. The obtained tablet had a hardness of 3.5 kp (n=5). In case of utilizing a sugar which did not change to amorphous state, it was confirmed that a tablet strength did not show a large increasing by a humidification and drying process.

EXPERIMENT 1

A stability of the tablet strength at a stored condition in the present invention was under examination. In the present experiment, the obtained tablet in Example 11 in the present invention was examined as the present invention tablet. To the contrally, regarding the obtained tablet in Comparative Example 1, the tablet was under a humidification and drying process to obtain a tablet (Example 1), or the tablet was before a humidification and drying process (Comparative Example 2). The condition for stored was at 25° C. (humidity 75%). FIG. 1 shows the result of the Experiment. FIG. 1 suggested that the preparation in the present invention has a stability of showing little changes in tablet strength under the stored at a moisture condition. To the contrally, it was found that the tablet strength in the Comparative Examples decreased down to the half of the initial strength by gradient from the time the experiment started. Therefore, the present invention is to provide a more stability against the moisture under the stored.

Industrial Feasibility

After the tablet of the present invention is processed by humidification and drying during the production process, the amorphous sugar irreversibly changes to crystalline state. It is stable with respect to the storage humidity. The tablet strength can be maintained in a stable manner. Furthermore, in the tablet of the present invention, it is possible to produce the sugar and the amorphous sugar of the present invention from one type of sugar. As a result, it is possible to design a tablet which takes into account the stability of the drug. Furthermore, in the tablet of the present invention, it is possible to provide a production method which uses the standard granulator and tablet machine.

In particular, in the production method of the present invention, wherein: sugar which is capable of becoming amorphous is dissolved in a medicinally permitted solvent; the solution is sprayed against drug and/or sugar (A); this is coated and/or granulated, a freeze dryer is not necessary. The present invention uses the granulator and tablet machine which is a widely accepted part tablet forming process. As a result, this is a valuable method because of its high production effeciency.

What is claimed is:

1. A quick disintegrating tablet in buccal cavity, said tablet produced by a method comprising:
    (i) forming a mixture comprising a pharmaceutically active ingredient, a sugar (A) and an amorphous sugar (B) into a tablet;
    (ii) humidifying said tablet to increase tablet hardness and stability; and
    (iii) drying said tablet, wherein said tablet hardness is about 3.1 kp or more.

2. A quick disintegrating tablet of claim 1, wherein said mixture is prepared by wet granulation.

3. The quick disintegrating tablet of claim 1, wherein said mixture is prepared by non-wet granulation.

4. The quick disintegrating tablet of claim 1, wherein said mixture is prepared by dry blending.

5. The quick disintegrating tablet of claim 1, wherein said sugar (B) is obtained by dissolving a crystalline sugar in a medicinally permitted solvent. and removing the solvent and drying.

6. The quick disintegrating tablet of claim 5, wherein said removing the solvent is carried out by spray drying or freeze drying.

7. The quick disintegrating tablet of claim 5, wherein said removing the solvent is carried out by a granulating method.

8. The quick disintegrating tablet of claim 6, wherein said granulating method is selected from the group consisting of fluidized-bed granulating method, vertical granulating method, and tumbling granulating method.

9. The quick disintegrating tablet of claim 1, wherein said sugar (A) and said amorphous sugar (B) are the same sugar.

10. The quick disintegrating tablet of claim 1, wherein said sugar (A) and said amorphous sugar (B) are different sugars.

11. The quick disintegrating tablet of claim 1, wherein said sugar (A) is selected from the group consisting of lactose, glucose, trehalose, mannitol and erythritol.

12. The quick disintegrating tablet of claim 1, wherein said amorphous sugar (B) is selected from the group consisting of glucose, lactose, maltose, sorbitol, trehalose, lactitol and fructose.

13. The quick disintegrating tablet of claim 1, wherein said sugar (A) is present in an amount comprising 50 weight/weight % or above, depending on the amount of pharmaceutically active ingredient.

14. The quick disintegrating tablet of claim 1, wherein said amorphous sugar (B) is present in an amount comprising 2 to 20 weight/weight % of said sugar (A).

15. The quick disintegrating tablet of claim 1, wherein said amorphous sugar (B) is present in an amount comprising 2 to 20 weight/weight % of the entire tablet.

16. The quick disintegrating tablet of claim 1, wherein said tablet disintegrates in a buccal cavity in 25 seconds or less.

17. The quick disintegrating tablet of claim 1, wherein said pharmaceutically active ingredient is present in an effective treatment amount comprising about 50 weight/weight % or below of the entire tablet.

18. The quick disintegrating tablet of claim 1, wherein said pharmaceutically active ingredient is present in an effective treatment amount comprising about 20 weight/weight % or below of the entire tablet.

19. The quick disintegrating tablet of claim 1, wherein said mixture of step (i) further comprises a taste-masking agent.

20. A process for producing a rapidly disintegrating tablet in buccal cavity, comprising:
(i) forming a mixture comprising a pharmaceutically active ingredient, a sugar (A) and an amorphous sugar (B) into a tablet;

(ii) humidifying to increase tablet hardness and stability; and (iii) drying said tablet, wherein said tablet hardness is about 3.1 kp or more.

21. The process of claim 20, wherein said mixture is prepared by wet granulation.

22. The process of claim 20, wherein said mixture is prepared by non-wet granulation.

23. The process of claim 20, wherein said mixture is prepared by dry blending.

24. The process of claim 20, wherein said sugar (B) is obtained by dissolving a crystalline sugar in a medicinally permitted solvent, and removing the solvent and drying.

25. The process of claim 24, wherein said removing the solvent is carried out by spray drying or freeze drying.

26. The process of claim 24, wherein said removing the solvent is carried out by a granulating method.

27. The process of claim 26, wherein said granulating method is selected from the group consisting of fluidized-bed granulating method, vertical granulating method, and tumbling granulating method.

28. The process of claim 20, wherein said sugar (A) and said amorphous sugar (B) are the same sugar.

29. The process of claim 20, wherein said sugar (A) and said amorphous sugar (B) are different sugars.

30. The process of claim 20, wherein said sugar (A) is selected from the group consisting of lactose, glucose, trehalose, mannitol and erythritol.

31. The process of claim 20, wherein said amorphous sugar (B) is selected from the group consisting of glucose, lactose, maltose, sorbitol, trehalose, lactitol and fructose.

32. The process of claim 20, wherein said sugar (A) is present in an amount comprising 50 weight/weight % or above, depending on the amount of pharmaceutically active ingredient.

33. The process of claim 20, wherein said amorphous sugar (B) is present in an amount comprising 2 to 20 weight/weight % of said sugar (A).

34. The process of claim 20, wherein said amorphous sugar (B) is present in an amount comprising 2 to 20 weight/weight % of the entire tablet.

35. The process of claim 20, wherein said tablet disintegrates in a buccal cavity in 25 seconds or less.

36. The process of claim 20, wherein said pharmaceutically active ingredient is present in an effective treatment amount comprising about 50 weight/weight % or below of the entire tablet.

37. The process of claim 20, wherein said pharmaceutically active ingredient is present in an effective treatment amount comprising about 20 weight/weight % or below of the entire tablet.

38. The process of claim 20, wherein said mixture of step (i) further comprises a taste-masking agent.

* * * * *